US008395008B2

(12) United States Patent
Ryu (10) Patent No.: US 8,395,008 B2
(45) Date of Patent: Mar. 12, 2013

(54) PROCESS AND CATALYST FOR CRACKING OF ETHERS AND ALCOHOLS

(75) Inventor: J. Yong Ryu, Pasadena, TX (US)

(73) Assignee: Catalytic Distillation Technologies, Pasadena, TX (US)

( * ) Notice: Subject to any disclaimer, the term of this patent is extended or adjusted under 35 U.S.C. 154(b) by 1002 days.

(21) Appl. No.: 12/260,729

(22) Filed: Oct. 29, 2008

(65) Prior Publication Data

US 2009/0178955 A1 Jul. 16, 2009

Related U.S. Application Data (60) Provisional application No. 61/020,883, filed on Jan. 14, 2008, provisional application No. 61/022,119, filed on Jan. 18, 2008, provisional application No. 61/094,676, filed on Sep. 5, 2008.

(51) Int. Cl.
    *C07C 1/20* (2006.01)
(52) U.S. Cl. .......................... 585/640; 585/638; 585/639
(58) Field of Classification Search .................. 585/638, 585/639, 640
    See application file for complete search history.

(56) References Cited

U.S. PATENT DOCUMENTS

| | | | |
|---|---|---|---|
| 3,619,412 A | 11/1971 | Clement et al. | |
| 3,816,297 A | 6/1974 | Liden et al. | |
| 4,324,698 A | 4/1982 | Lewis et al. | |
| 4,395,580 A * | 7/1983 | Juguin et al. | 585/639 |
| 4,398,051 A | 8/1983 | Araki et al. | |
| 4,447,668 A * | 5/1984 | Smith et al. | 585/639 |
| 4,691,073 A | 9/1987 | Michaelson | |
| 4,871,446 A | 10/1989 | Herbst et al. | |
| 4,880,787 A | 11/1989 | Bundens et al. | |
| 4,888,103 A | 12/1989 | Herbst et al. | |
| 5,043,518 A | 8/1991 | Michaelson et al. | |
| 5,043,519 A | 8/1991 | Orfeo et al. | |
| 5,227,564 A | 7/1993 | Chen et al. | |
| 5,811,620 A * | 9/1998 | Knifton et al. | 585/639 |
| 5,817,871 A | 10/1998 | Dingerdissen et al. | |
| 5,840,988 A | 11/1998 | Eller et al. | |
| 6,046,373 A * | 4/2000 | Sun | 585/640 |
| 7,026,266 B2 * | 4/2006 | Chaudhari et al. | 502/155 |
| 2005/0197520 A1 | 9/2005 | Mertens et al. | |

FOREIGN PATENT DOCUMENTS

| | | |
|---|---|---|
| CN | 1432431 A | 7/2003 |
| CN | 1853772 A | 11/2006 |
| EP | 1783099 A1 | 5/2007 |

OTHER PUBLICATIONS

English Translation of CN 1853772, Nov. 2006.*
English Translation of CN 1432431, Jul. 2003.*
Examination Report issued Jan. 17, 2011 by the Danish Patent Office in corresponding Singapore Patent Application No. 200900228-8 (9 pages).
Written Opinion issued May 12, 2010 by the Danish Patent Office in corresponding Singapore Patent Application No. 200900228-8 (9 pages).
International Preliminary Report on Patentability dated Jul. 20, 2010 issued by The International Bureau of WIPO on corresponding application No. PCT/US2009/030425 (5 pages).
Search Report with Written Opinion for related Singapore Application No. 200900228-8 dated Jul. 2, 2009. (7 pages).
International Search Report with Written Opinion for related Application No. PCT/US2009/030425 dated Aug. 12, 2009. (9 pages).
First Office Action (with translation) dated Mar. 31, 2012 in corresponding Chinese application No. 200910003602.1 (20 pages).
English translation of CN 1853772, Nov. 2006 (15 pages).
English translation of CN 1432431, Jul. 2003 (15 pages).
Invitation to Respond to Written Opinion issued Jun. 25, 2012 in corresponding Singapore application No. 201102190-4 together with Written Opinion and Search Report issued May 25, 2012 by the Hungarian Intellectual Property Office (15 pages).
Official Letter with Search Report (translated) issued Sep. 13, 2012 in corresponding Taiwan (R.O.C.) Patent Application No. 098100917 (7 pages).

* cited by examiner

*Primary Examiner* — Elizabeth Wood
(74) *Attorney, Agent, or Firm* — Osha • Liang LLP (57) ABSTRACT

A process for the production of olefins from at least one of an alcohol and ether, the process including: contacting at least one alcohol or ether with a hydrofluoric acid-treated amorphous synthetic alumina-silica catalyst under decomposition conditions to produce an olefin. Also disclosed is a process for the production of isobutylene from methyl tertiary butyl ether, the process including: feeding methyl tertiary butyl ether (MTBE) to a reactor having at least one reaction zone containing a hydrofluoric acid-treated amorphous synthetic alumina-silica catalyst; contacting the MTBE with the hydrofluoric acid-treated amorphous synthetic alumina-silica catalyst under decomposition conditions to produce a reactor effluent comprising isobutylene, unreacted MTBE, heavies, and methanol; feeding the reactor effluent to a first distillation column; separating the isobutylene from the unreacted MTBE, heavies, and the methanol in the first distillation column to recover a first bottoms fraction comprising heavies, unreacted MTBE, and methanol and an isobutylene-rich overheads fraction.

23 Claims, 4 Drawing Sheets

PROCESS AND CATALYST FOR CRACKING OF ETHERS AND ALCOHOLS

CROSS-REFERENCE TO RELATED APPLICATION

This application, pursuant to 35 U.S.C. §119(e), claims priority to U.S. Provisional Application Ser. No. 61/020,883, filed Jan. 14, 2008, U.S. Provisional Application Ser. No. 61/022,119, filed Jan. 18, 2008, and U.S. Provisional Application Ser. No. 61/094,676, filed Sep. 5, 2008. Each of these applications is incorporated by reference in its entirety.

BACKGROUND OF DISCLOSURE

1. Field of the Disclosure

Embodiments disclosed herein relate generally to catalysts and processes for the decomposition of ethers and alcohols to form olefins. More specifically, embodiments disclosed herein relate to hydrofluoric acid treated amorphous synthetic alumina-silica catalysts useful for the decomposition of ethers, such as alkyl tertiary-alkyl ethers, to form olefins, such as tertiary olefins.

2. Background

Ethers may be decomposed to corresponding olefins and alcohols in the presence of an acid catalyst. For example, alkyl tertiary-alkyl ethers, such as methyl tertiary-butyl ether (MTBE) or tertiary-amyl methyl ether (TAME) may be cracked to tertiary olefins and corresponding alcohols over an acidic solid catalyst. The resulting olefin products, isobutylene and isoamylenes, are important raw materials for various applications. Isobutylene, for example, is a raw material for production of synthetic rubber. Isoamylene is a raw material for various specialized applications, such as herbicides, flavors, fragrances, and a copolymerization agent, among others.

One major difficulty encountered in the catalytic cracking of alkyl tertiary-alkyl ethers is a relatively short catalyst cycle length, generally caused by polymer deposition on the catalyst due to the highly reactive nature of the tertiary olefins. Additionally, a very small amount of dienes or diene-precursors may be detrimental to catalyst longevity. Thus, dienes and diene-precursors in feed streams are typically removed by hydrogenation, distillation, or both.

Various natural clays are acidic materials that can serve as catalysts for acid catalyzed chemical reactions, such as the cracking of alkyl tertiary-alkyl ethers. Clays are naturally occurring crystalline phyllosilicate minerals (mostly aluminosilicates) with various impurities. Aluminum, magnesium, calcium, sodium, and the like, are important cationic components of layered silicate minerals. When these cationic species, especially mono and divalent cations, are removed by proper chemical means, Brönstead acidic sites are introduced to the clay materials, and they can serve as acidic catalysts for various chemical reactions.

Many clays have layered or ordered structures. For example, kaolin, montmorillonite, attapulgite, bentonite, beidellites, and other clays have layered structures. When such clays are properly treated, they become quite acidic. As a means to increase catalytic active sites, pillars may be introduced between the clay layers in addition to creating acidic sites. This pillaring technique multiplies the number of catalytic acidic sites.

Both acidic clays and synthetic aluminosilicates have been used as a matrix for producing fluid catalytic cracking (FCC) catalysts. Calcined kaolin has been utilized as a raw material in the synthesis of Y-zeolite in microsphere form. Additionally, dehydration of ethanol to ethylene over mixed oxides of alumina-silica and alumina catalysts was studied by J. Koubek et al., Proceedings of the $7^{th}$ International Congress on Catalysis, Part B, 853, 1980.

U.S. Pat. No. 4,398,051 discloses obtaining high purity tertiary olefins, such as isobutylene, by decomposition of alkyl-tertiary-alkyl ethers over acidic catalysts. The catalyst used was an alumina compound supported on a carrier containing silicon dioxides. The alumina compound on a support is decomposed by calcining at high temperatures (750-1000° C.). The carriers included silica, montmorillonite, kaolinite, attapulgite, silica-zirconia, and others. However, no data regarding catalyst stability or catalyst deactivation is presented.

U.S. Pat. Nos. 5,043,518 and 4,691,073 disclose a process using clay catalysts for producing isoamylenes by cracking TAME over various natural clay catalysts, such as attapulgite clay, treated with an aqueous hydrofluoric acid (HF) solution. Benefits disclosed by treating the natural clays with HF include a higher activity and increased catalyst stability, which are measured in terms of cracking temperature required to maintain 95% conversion of TAME. This type of clay is also an effective catalyst for the production of isobutylene from MTBE. These patents also mention use of synthetic clays in passing, and do not present any data directed toward synthetic clays.

Commercially, attapulgite clay catalysts are sold as granules. Unfortunately, attapulgite clay catalysts do not have good physical integrity. Additionally, HF treatment further weakens the physical integrity, which is measured by attrition rate or crushing strength. As a result, the HF treated attapulgite clays must be handled with care, and the catalyst life is typically no more than 6 months.

Other downfalls of HF treated attapulgite clays include disposal costs. Such catalysts must be treated or otherwise rendered inert prior to disposal, adding to the cost of producing tertiary olefins. Additional costs are encountered by the large amount of HF required for the clay treating process, increasing raw material costs and creating a large amount of fluorinated waste solution. Although the HF treated attapulgite generates a lot of waste materials, the service time and deactivation are a significant improvement over untreated clay catalysts.

Another downside to use of HF treated clays includes increased production of byproducts, such as dimethyl ether (DME). Because of the higher catalytic activity of HF treated clays, they produce, in general, more DME than untreated clay catalysts. Catalyst deactivation typically results in a lower conversion of alkyl tertiary-alkyl ethers, such that the cracking temperature is raised to maintain a steady conversion as the catalyst deactivates. As treated attapulgite clay catalysts deactivate at a slower rate than untreated catalyst, the slower temperature ramping does not affect DME production as much as for untreated clay catalysts. Decreased DME production is a desired benefit not generally obtained with HF treated attapulgite clays.

U.S. Pat. No. 5,043,519 ('519) discloses a process for the production of tertiary olefins by decomposing alkyl tertiary-alkyl ethers in the presence of a catalyst containing 0.1 to 1.5 weight percent alumina on silica. As disclosed, at least 0.5 weight percent alumina is required for slower catalyst deactivation, and addition of small quantities of water into the feed stream may suppress DME formation. Nevertheless, the experimental results presented in Table 2 of the '519 patent shows more than about 1800 ppm DME by weight in the product stream at about 75% MTBE conversion, and more than 4500 ppm DME at a slightly higher conversion of 76.8%.

U.S. Pat. Nos. 4,880,787, 4,871,446, 4,888,103, and 4,324,698 each mention that amorphous silica-alumina catalysts are useful as cracking catalysts. However, as noted in U.S. Pat. No. 4,880,787, the major conventional cracking catalysts in use at that time (late 1980's, early 1990's), the same time period as the aforementioned U.S. Pat. No. 4,691,073, generally incorporated a large pore crystalline aluminosilicate. To the present inventor's knowledge, commercial synthetic silica-alumina catalysts for cracking remain to this day to be of a crystalline nature.

Accordingly, there exists a need for improved catalysts for the production of tertiary olefins. Such improved catalysts are desired to have one or more of an increased cycle length, good physical integrity, a low attrition rate, a high crushing strength, decreased production costs, and decreased disposal costs.

SUMMARY OF THE DISCLOSURE

In one aspect, embodiments disclosed herein relate to a process for the production of olefins from at least one of an alcohol and an ether, the process including: contacting at least one of an alcohol and an ether with a hydrofluoric acid-treated amorphous synthetic alumina-silica catalyst under decomposition conditions to produce an olefin.

In another aspect, embodiments disclosed herein relate to a process for the production of isobutylene from methyl tertiary butyl ether, the process including: feeding methyl tertiary butyl ether (MTBE) to a reactor having at least one reaction zone containing a hydrofluoric acid-treated amorphous synthetic alumina-silica catalyst; contacting the MTBE with the hydrofluoric acid-treated synthetic alumina-silica catalyst under decomposition conditions to produce a reactor effluent comprising isobutylene, unreacted MTBE, heavies, and methanol; feeding the reactor effluent to a first distillation column; separating the isobutylene from the unreacted MTBE, heavies, and the methanol in the first distillation column to recover a first bottoms fraction comprising heavies, unreacted MTBE, and methanol and an isobutylene-rich overheads fraction.

In another aspect, embodiments disclosed herein relate to a catalyst useful for the decomposition of ethers and alcohols to form olefins, the catalyst comprising a hydrofluoric acid-treated amorphous synthetic alumina-silica catalyst.

In another aspect, embodiments disclosed herein relate to a process for the production of olefins from at least one of an alcohol and an ether, the process comprising: contacting at least one of an alcohol and an ether with a selectively poisoned amorphous synthetic alumina-silica catalyst under decomposition conditions to produce an olefin.

Other aspects and advantages will be apparent from the following description and the appended claims.

DETAILED DESCRIPTION

In one aspect, embodiments disclosed herein relate to a process for the production of olefins from ethers and alcohols, and catalysts therefore. In another aspect, embodiments disclosed herein relate to a process for the production of catalysts useful for the cracking of ethers and alcohols to form olefins.

Catalysts useful in embodiments disclosed herein include amorphous synthetic alumina-silica catalysts. In some embodiments, catalysts useful in embodiments disclosed herein include hydrofluoric acid (HF) treated amorphous synthetic alumina-silica catalysts. Amorphous synthetic alumina-silica catalysts may be prepared by co-precipitation or impregnation techniques, followed by drying and calcination. The amorphous alumina-silica materials may contain from about 0.1 to about 99 weight percent silica in some embodiments; from about 1 to about 98 weight percent silica in other embodiments; from about 2 to about 98 weight percent silica in other embodiments; from about 2 to about 97 weight percent silica in other embodiments; and from about 3 to about 96 weight percent silica in yet other embodiments. Although described herein as amorphous, alumina-silica materials useful in embodiments described herein may contain a minor amount of crystalline alumina, depending on the source of the alumina material used to prepare the precipitated alumina-silica precursor, the amount of the alumina in the alumina-silica, as well as the calcination temperature.

The catalysts may also contain one or more optional elements, including titanium, zirconium, hafnium, tantalum, and niobium, in an amount from about 0 weight percent up to about 10 weight percent; from about 0.01 weight percent to about 3 weight percent in other embodiments. These optional elements may be incorporated into the catalyst material prior to HF treatment or introduced to the material after HF treatment.

The HF treated amorphous synthetic alumina silica catalysts useful in embodiments disclosed herein may be prepared by treating amorphous synthetic alumina-silica with a dilute aqueous HF solution at ambient temperature. The amount of HF required for the treatment depends on the detailed composition of a given amorphous synthetic alumina and its physical properties. In general, the amount of anhydrous hydrofluoric acid used during the treating step may range from greater than 0 g to about 65 g per kg of alumina-silica. For dilute HF solutions, such as a 50% HF solution, the amount of dilute HF should be adjusted accordingly; for the 50% HF, for example, the amount of 50% HF solution may range from greater than 0 g to about 130 g per kg of alumina-silica. In other embodiments, the amount of anhydrous hydrofluoric acid used during the treating step may range from about 10 g to about 40 g per kg of alumina-silica (20 g to 80 g per kg alumina-silica for a 50% HF solution). HF solutions, used at the above ratios, may be diluted with additional water so as to completely immerse the entire volume of alumina-silica to be treated in dilute HF.

It is additionally noted that the above ratio of HF to amorphous alumina-silica is significantly less than the ratio of HF to attapulgite clay typically used in forming HF treated attapulgite clays, as described above. Thus, the HF treated amorphous synthetic alumina-silica catalysts described herein may be environmentally more disposable. Additionally, less fluorinated waste solution may be generated. Each of these may contribute to a decrease in raw material and disposal costs for catalyst manufacture.

The amorphous alumina-silica may be contacted with the diluted HF solution for a time ranging from 5 minute to 2 hours in some embodiments; from 15 minutes to 90 minutes in other embodiments. The treating may be performed at a temperature from room temperature to about 90° C., and the slurry may be stirred continuously or intermittently. The HF treatment of amorphous synthetic alumina-silica catalysts may be performed in a single step or multiple steps.

Following HF treatment, the excess solution in the treatment vessel should be drained, and the HF treated amorphous synthetic alumina-silica may be washed with sufficient amounts of clean, deionized water. The catalyst may then be dried and calcined prior to use as a catalytic material. Calcining may be performed at a temperature from 300° C. to 850° C. in some embodiments; at a temperature ranging from 400° C. to 750° C. in other embodiments.

Amorphous synthetic alumina-silica catalysts and HF treated amorphous synthetic alumina-silica catalysts according to embodiments disclosed herein may have a high activity, which may result in the production of undesired byproducts, such as isoalkanes and ethers. Isoalkane byproducts may undesirably complicate product purification/separations as the boiling points of the isoalkanes are similar to that of the tertiary olefins. Additionally, while HF treatment may result in catalysts having a higher activity and longer cycle times than untreated amorphous synthetic alumina-silica catalysts, polymer deposition and byproduct production may remain problematic.

Selective poisoning of strongly acid sites on both amorphous synthetic alumina-silica catalysts and HF treated amorphous synthetic alumina-silica catalysts may improve catalyst selectivity, reducing both production of unwanted byproducts and formation of polymers, thus further resulting in extended catalyst cycle times. Selective poisoning and related terms (selectively poisoned, etc.) as used herein refers to the treatment of the catalyst to neutralize (poison) unwanted acid sites in the catalyst structure having a high acidity or sites of unnecessarily too strong acid strength. The selectively poisoned catalysts disclosed herein may thus have a moderate acidity or mild acidity or both, in general terms, as a whole, as the acid sites having a comparatively high acidity and/or unwanted sites are selectively poisoned.

Selective poisoning of catalysts disclosed herein may be performed by treating the catalysts with one or more compounds that may react or interact with strong acidic sites and/or unwanted catalytic sites within the catalyst. Examples of compounds useful for selective poisoning may include alkali metal compounds, alkaline earth compounds, bismuth compounds, and other basic compounds known to those skilled in the art. Such compounds may include elements, which are effective for selective poisoning, including Na, K, Rb, Cs, Mg, Ca, Cu, Pb, Cr. Be, Sn, Sr, Ba, Zn, Fe, Ti, Bi, Mo, Mn, La, Ce, and Ac, among others.

The amount of the selective poisoning element or elements contacted with and reacted onto the amorphous synthetic alumina-silica may depend on the nature of intended reaction (or specific reactant), specific catalyst compositions, and the specific element used for poisoning. The amount of metal elements on a catalyst for selective poisoning may be within the range from about 5 ppm to about 8% by weight in some embodiments; from about 10 ppm to about 4% by weight in other embodiments. In various embodiments, the compounds used for treating a catalyst can be either an inorganic or organic salt or organometallic compound metal hydroxide. The poisoning may be performed in aqueous medium, organic medium or a mixed medium of water and an organic solvent.

To selectively poison amorphous synthetic alumina-silica catalysts according to embodiments disclosed herein, the catalyst may be treated with an aqueous or organic solution of a compound or compounds useful for selectively poisoning at a temperature in the range from about 0° C. to about 200° C. in some embodiments; at a temperature from about 10° C. to about 125° C. in other embodiments. The treating method can be any method as long as it produces the intended result, namely the selective poisoning of highly acidic and/or unwanted sites, examples of which include ion-exchange methods, impregnation, soaking, refluxing, etc. After contact with the selective poisoning compound or compounds, the selectively poisoned catalyst may be washed with a solvent, such as water, alcohol, acetone, or a mixture thereof, and dried. After drying, the catalyst may be calcined at a temperature in the range from about 150° C. to about 800° C. in some embodiments, from about 200° C. to about 600° C. in other embodiments, for a period of time in the range from about 5 minutes to about 24 hours, such as from about 15 minutes to about 6 hours.

Alternatively, selective poisoning of the catalyst may be performed in situ. For example, a small amount of a basic compound may be added into the decomposition reactor with a feed stream. The basic compound added may be non-reactive with the hydrocarbons present under reaction condition and should not interfere with the separation and recovery of the desired reaction products (i.e., selectively poisoning the catalyst while not interfering with the desired hydrocarbon processing). Examples of basic compounds that may be added for poisoning of the catalyst in situ may include ammonia and dimethyl ether, among others.

The above described HF treated amorphous synthetic alumina-silica catalysts, selectively poisoned amorphous synthetic alumina-silica catalysts, and selectively poisoned HF treated amorphous synthetic alumina-silica catalysts may be used to produce various olefins from ethers and alcohols. Various olefins which may be obtained according to processes described herein include ethylene, propylene, isobutylene, isoamylenes such as 2-methyl-2-butene and 2-methyl-1-butene, isohexenes, such as 2,3-dimethyl-1-butene, 2,3-dimethyl-2-butene, 2-methyl-1-pentene, 2-methyl-2-pentene, (cis and trans) 3-methyl-2-pentene, 2-ethyl-1-butene and 1-methyl-cyclopentene, and the tertiary isoheptenes. Such olefins may be produced from suitable alkyl tertiary-alkyl ethers, tertiary alcohols, sec-alkyl ethers, primary alcohols, and mixtures thereof. For example, isobutylene may be produced by decomposing one or more of MTBE, ethyl tertiary-butyl ether (ETBE), and tertiary butyl alcohol (TBA). Isoamylene may be produced by decomposing TAME or tertiary-amyl ethyl ether (TAEE). Propylene may be produced by decomposing diisopropyl ether (DIPE), isopropyl alcohol (IPA), or mixtures thereof. In other embodiments, secondary alcohols may also be used.

As further examples, ethylene may be produced by dehydrating ethanol or a mixture of ethanol and diethyl ether. So-called "renewable ethylene" may be produced by dehydrating bio-ethanol. Additionally, diethyl ether may be produced by dehydrating ethanol. The diethyl ether by-product may be recovered from the reactor effluent stream and recycled as part of the feed mixture. Catalysts described above may also be used for the dehydration of methanol to produce dimethyl ether (DME), which may be used in or as diesel fuels.

Catalysts and processes described herein are also useful in the production of high purity isobutylene by decomposing MTBE, TBA, or mixtures thereof. Decomposing a mixture of MTBE with a minor amount of TBA to produce isobutylene may be preferred over MTBE alone as less undesirable by-products, such as isobutane, DME, and diisobutylene, are produced.

Optionally, a small amount of water or water equivalents may be added with the feed to suppress unwanted side reactions. As used herein, "water equivalents" refers to water added to the reactor directly or to water added to the reactor indirectly, such as by decomposition of an alcohol to form water and an olefin, where the alcohol may be used in an amount sufficient to result in an equivalent amount of water in the reactor. For example, in the alternative to adding water to the feed when decomposing MTBE, feed of TBA to the reactor, and the subsequent decomposition of the TBA, will produce a similar olefin, isobutylene, with the co-production of water. The amount of water equivalents used in various embodiments may range from 0.1 to 5 weight percent; up to 3 weight percent water in other embodiments, up to 1.0 weight percent in other embodiments, where the above values are based on the total weight of water equivalents and the ether feed.

Addition of water or TBA to an MTBE feed stream, for example, may be beneficial during the early stage of MTBE decomposition to suppress unwanted side reactions. As the catalyst slowly deactivates, the amount of water or TBA addition may be slowly reduced.

The cracking reaction (also referred to herein as decomposition or dehydration) may be performed in one or more fixed bed reactors in the presence of a catalyst disclosed in this invention such as an HF treated amorphous synthetic alumina-silica catalyst as described above. Examples of fixed bed reactors useful in embodiments disclosed herein may include tubular reactors, boiling point reactors, bubble column reactors, traditional fixed bed reactors, catalytic distillation columns, divided wall distillation column reactors, pulsed flow reactors, and combinations thereof. One or more of such reactors may be used in parallel flow or series flow.

Decomposition reaction conditions may vary based on the feed mixture used and the desired olefins produced. Decomposition temperatures may range from 100° C. to 500° C. in some embodiments; from 130 to 350° C. in other embodiments and from 150° C. to 300° C. in yet other embodiments. The decomposition reaction may be carried out under pressures in the range from 1 to 22 bar (0 to 300 psig) in some embodiments; from 1 to 11 bar (0 to 150 psig) in other embodiments. In some embodiments, the pressure is maintained such that the product olefin is in the liquid phase or partially in the liquid phase at the reaction temperature used. The liquid hourly space velocity (LHSV) (the volume of liquid per volume of catalyst per hour) at which the reaction is carried out may be within the range from 0.5 to 200 h$^{-1}$ in some embodiments; from 1 to 50 h$^{-1}$ in other embodiments; and from 1 to 10 h$^{-1}$ in yet other embodiments.

Contact of the alcohol and/or ether feed with catalysts as described herein, at decomposition conditions, may result in the production of the desired olefin, alcohols, and heavies, which may include by-product ethers, alcohols, and oligomers, such as a dimer or trimer of the desired olefin product. In some embodiments, contact of an ether feed with catalysts as described herein may result in conversion of at least 90 weight percent of the ether; at least 85 weight percent in other embodiments; at least 80 weight percent in other embodiments; at least 75 weight percent in other embodiments; and at least 70 weight percent in other embodiments.

Catalysts disclosed herein may maintain their catalytic activity for an extended service life. For example, catalysts disclosed herein may maintain a conversion of at least 65 weight percent of an ether feed for at least 9 months in some embodiments; at least 1 year in other embodiments; at least 15 months in other embodiments; at least 18 months in other embodiments; and up to 2 years or more in yet other embodiments.

Catalysts and processes disclosed herein may be used to produce and recover a high purity olefin product stream. For example, in some embodiments, a desired olefin may be recovered in an olefin-rich stream (as used herein, a stream rich in a particular component comprises at least 50 weight percent of said component). In other embodiments, the recovered olefin-rich fraction may have an olefin content greater than 90 weight percent; greater than 95 weight percent in other embodiments; greater than 97 weight percent in other embodiments; greater than 98 weight percent in other embodiments; greater than 98.5 weight percent in other embodiments; greater than 99 weight percent in other embodiments; greater than 99.1 weight percent in other embodiments; and greater than 99.5 weight percent in yet other embodiments. In other embodiments, the olefins recovered may be useful as a polymerization feedstock, having a purity of at least 99.8 weight percent.

Figure 1:
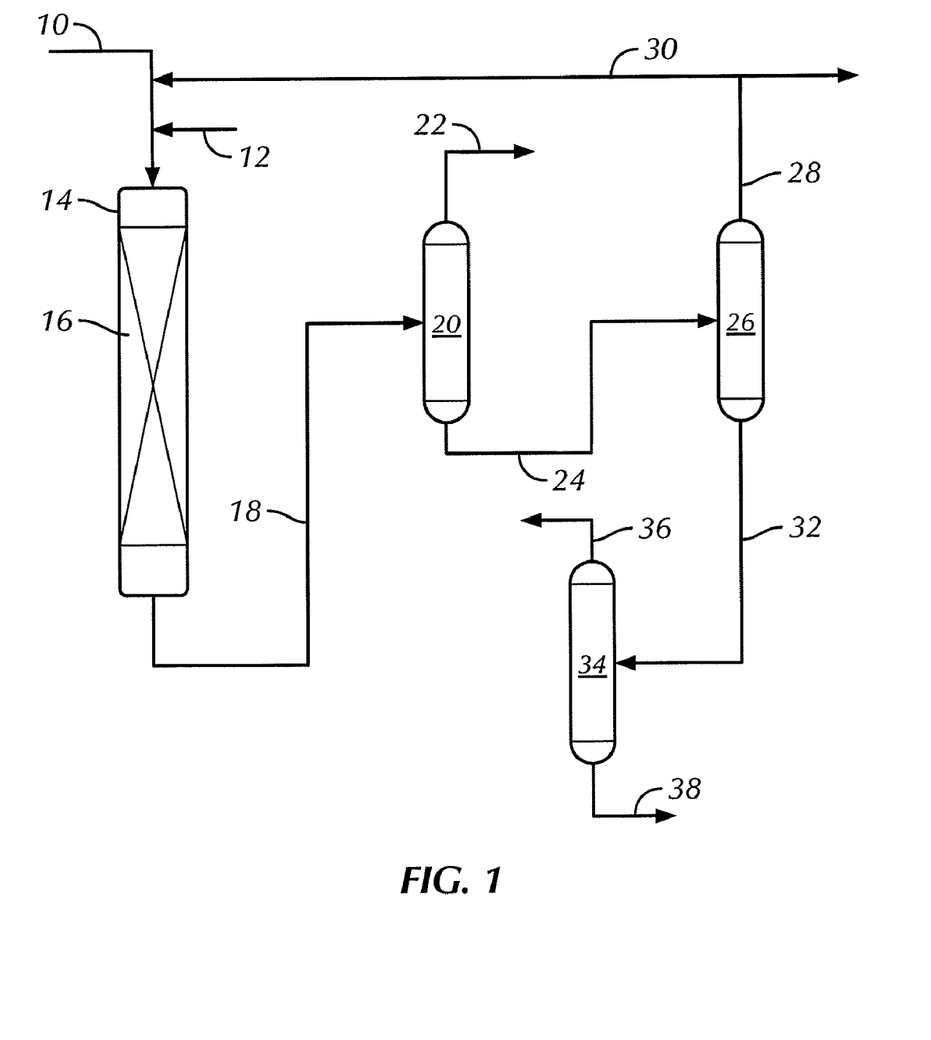
FIG. 1 is a simplified process flow diagram for producing tertiary olefins according to embodiments disclosed herein.

Referring now to FIG. 1, a simplified process flow diagram for the production of isobutylene from MTBE using the catalysts described herein is illustrated. Similar flow schemes may be used for the production of other olefins from feed stocks as described above, and will not be detailed herein.

MTBE feed 10 and optional water or TBA feed 12 are introduced to a fixed bed decomposition reactor 14. Decomposition reactor 14 may include one or more beds 16 of an HF treated amorphous alumina-silica catalysts as described herein. The MTBE may be contacted with the HF treated amorphous alumina-silica catalyst under decomposition conditions to produce a reactor effluent 18, which may include one or more of unreacted MTBE, heavies (such as diisobutylene and other heavier oligomers and by-products), methanol, and the desired product, isobutylene.

Reactor effluent 18 may be fed to a first distillation column 20 to separate and recover the isobutylene. The isobutylene may be separated from unreacted MTBE, methanol, and heavies, recovering an isobutylene-rich overhead fraction via flow line 22. Isobutylene-rich overheads, in some embodiments, may be a high purity isobutylene stream, having a concentration of at least 99.5 weight percent isobutylene.

The unreacted MTBE, methanol, and heavies may be recovered as a bottoms fraction from distillation column 20 and fed via flow line 24 to a second distillation column 26, where the unreacted MTBE may be separated from the heavies and the methanol. The unreacted MTBE may be recovered as an MTBE-rich overheads fraction via flow line 28, a portion of which may be recycled via flow line 30 to reactor 14 in some embodiments.

The heavies and methanol may be recovered as a bottoms fraction from distillation column 26 via flow line 32. If desired, the methanol may be recovered from the heavies, such as by feeding the heavies and methanol in flow line 32 to third distillation column 34. A methanol-rich overheads fraction may be recovered via flow line 36 and a heavies-rich bottoms fraction may be recovered via flow line 38.

As mentioned above, similar flow schemes to that presented in FIG. 1 may be used for the production of other olefins from feed stocks as described above. For example, additional reactors may be used, or additional separations may be required where the feed includes a mixture of ethers and/or alcohols resulting in the production of more than one desired olefin.

It is further noted that various schemes to recycle and reuse various reaction by-products may be used, promoting the overall conversion of the feed to the desired olefin. For example, diethyl ether produced as a by-product from the dehydration of ethanol may be recovered from the reactor effluent stream and recycled as part of the feed mixture.

The type of reactors for the decomposition of ethers and alcohols to olefins or for the dehydration of alcohols to ethers according to embodiments disclosed herein is not limited to any particular physical device. Any decomposition and dehydration reaction in the presence of the catalysts disclosed herein can be carried out in any physical device. Examples of suitable reactors for the decomposition of ethers and alcohols, and dehydration of alcohols to ethers may include traditional fixed bed tubular reactors, distillation column reactors, boiling point pulse flow reactors, and divided wall distillation column reactors, among others.

The reactions may be carried out in the vapor phase, liquid phase, or dual phase of liquid and vapor. Because of the equilibrium nature of the reactions, carrying out the reactions in the vapor phase or dual phase of vapor and liquid may result in a higher conversion per pass or higher olefin productivity than a liquid phase reaction, which may also require higher pressure.

Figure 4:
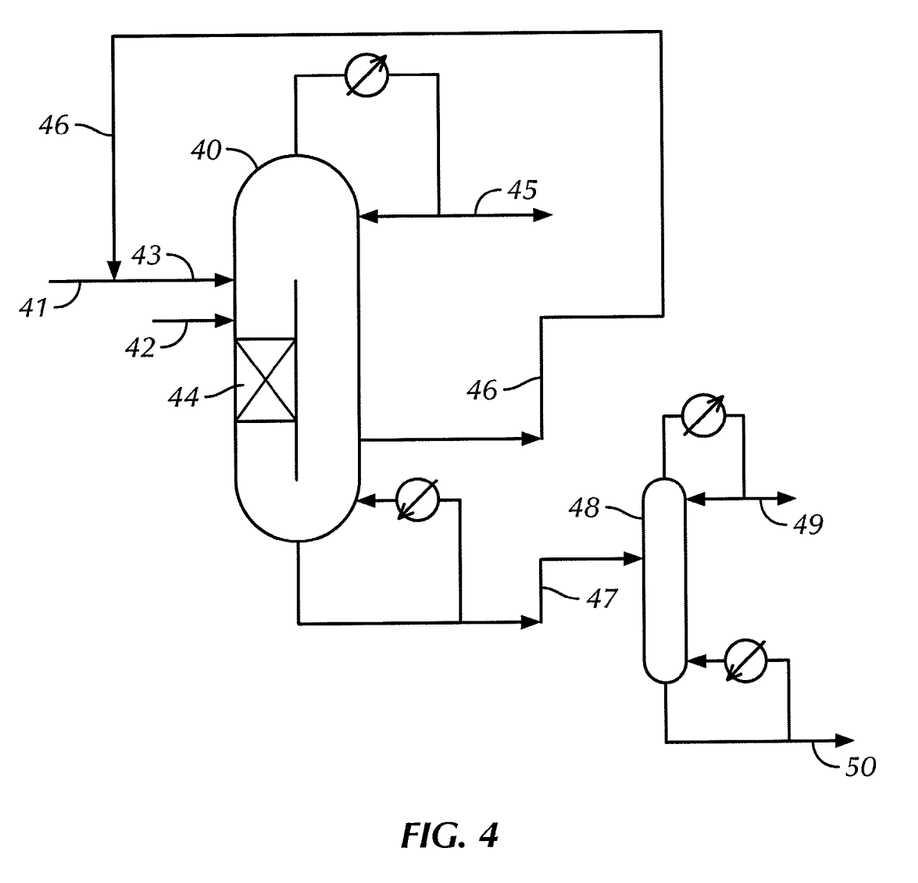
FIG. 4 is a simplified process flow diagram for producing tertiary olefins according to embodiments disclosed herein.

In some embodiments, olefins may be produced according to embodiments disclosed herein by carrying out the reactions in a catalytic divided wall distillation column, such as illustrated in FIG. 4. FIG. 4 illustrates a simplified process flow diagram for the catalytic decomposition of MTBE by using a divided wall distillation column. MTBE feed 41 is introduced to a proper position above catalytic reaction zone 44 in a catalytic divided wall distillation column 40 via line 43. A small stream 42 of water or TBA is also introduced to the column 40 above the catalyst zone 44. The decomposition product isobutylene is removed from the column 40 as overhead steam 45 along with minor amounts of by-products, including DME and isobutane. The isobutylene in stream 45 may be recovered as better than 99.5% purity product, as described above, by use of various separation schemes, such as distillation (not shown). The unreacted MTBE may be recovered by a side-draw stream 46 from the column 40 and recycled back via line 43. The bottom stream 47 from the column 40 includes methanol, water and heavies, and may be introduced to a distillation column 48 to recover methanol as overhead stream 49. The bottom stream 50, including the heavies and water, may be treated and disposed.

EXAMPLES

All MTBE decomposition reactions in the following Examples are carried out in a down flow reactor having a fixed bed of catalyst ½ inches in diameter and 21 inches long. The reactor has top and bottom heating zones, which are separately controlled. The fixed bed reactor is mounted vertically. The volume of solid catalysts tested was approximately 15 ml for each.

Comparative Example 1

A granular attapulgite clay (16 to 30 mesh) is calcined at 500° C. for 2 hours. This calcination is necessary to maintain physical integrity of the clay granules during aqueous hydrofluoric acid (HF) treatment.

A fluorinated attapulgite clay catalyst is prepared according to the procedure disclosed in U.S. Pat. No. 4,691,073. 34.2 grams calcined attapulgite clay granules is treated in an aqueous HF solution prepared by diluting 6.95 grams of 50% HF with 61.5 grams deionized water at ambient temperature for 1 hour with occasional stirring. After decanting out the excess solution, the clay is washed twice with 80 ml deionized water. The wet clay is dried at 100° C. in a vacuum oven for 1 hour and then calcined at 500° C. for 2 hours. This calcined catalyst is referred to herein as "F-ATT-1." The physical properties of the resulting catalyst are 151 $m^2$/g BET; 0.386 cc/g total nitrogen adsorption/desorption pore volume; and an average pore diameter of 10.2 nm.

Figure 2:
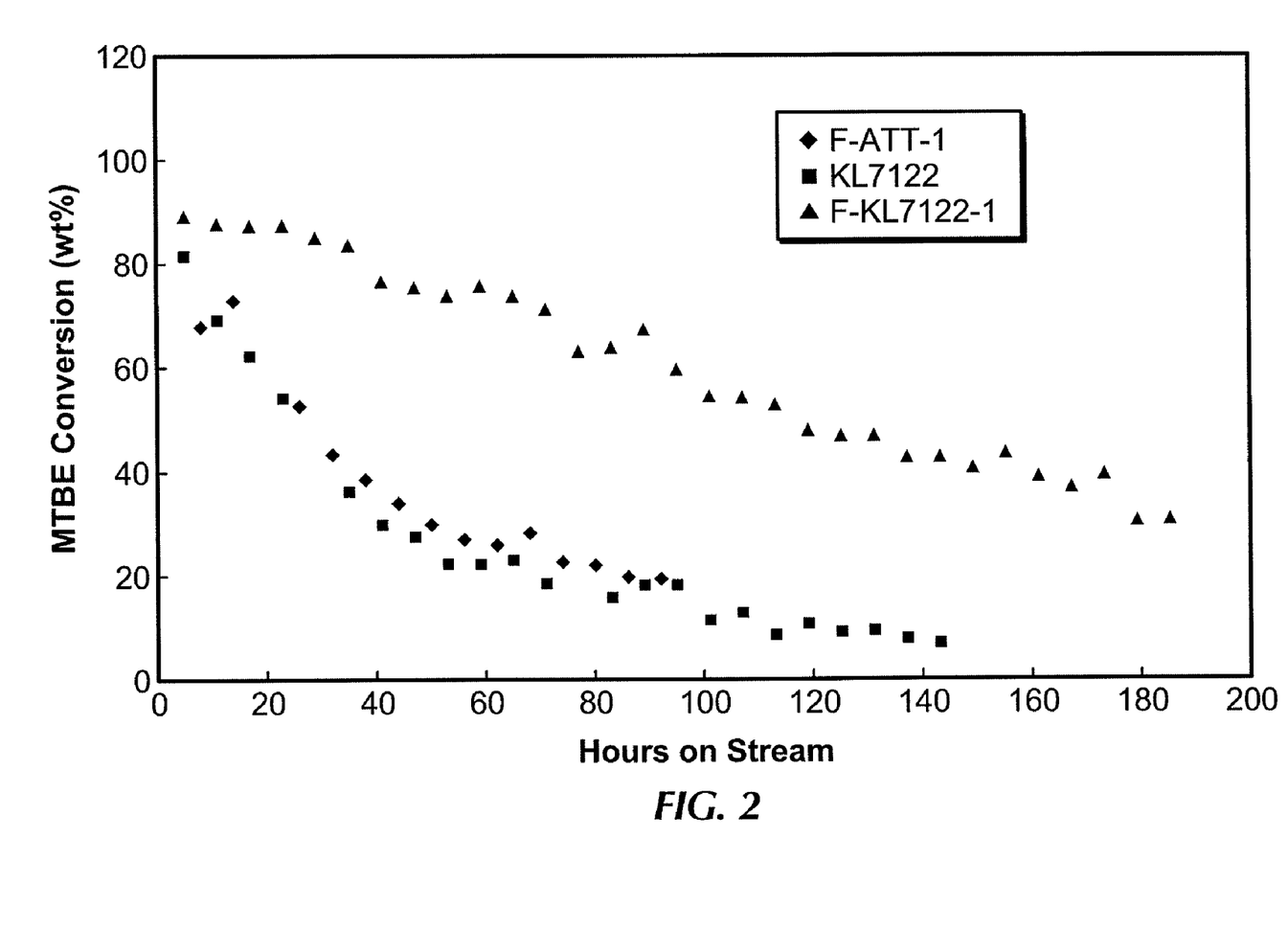
FIG. 2 is a graphical comparison of the catalyst activity, as measured by MTBE conversion, of catalysts according to embodiments disclosed herein as compared to prior art catalysts.

15 ml of F-ATT-1 catalyst is loaded in the reactor described above and tested with a crude mixed MTBE feed stock containing 95.9 wt. % MTBE. The feed also contains small amounts of highly unsaturated compounds such as 1,3-butadiene, trans-1,3-pentadiene, cis-1,3-pentadiene, 2-methyl-1,3-butadiene, and others. The test condition is 31 psig, 290° F., and 2.0 liquid hourly space velocity (LHSV) feed down-flow rate. The result of the test is illustrated in FIG. 2.

Comparative Example 2

A alumina-silica catalyst is prepared by co-precipitation method. The dried alumina-silica powder is extruded to 3 mm pellets, which are calcined at about 500° C. for 2 hours. The pellets are ground to 12-14 mesh granules. The granular alumina-silica catalyst contained 20% silica. This catalyst is referred to herein as "KL7122." The physical properties of the catalyst are 379.2 $m^2$/g BET; 0.646 cc/g total nitrogen adsorption/desorption pore volume; and an average pore diameter of 6.89 nm.

15 ml of KL7122 catalyst is tested under identical conditions as given for Comparative Example 1, with the same reactor and feed. The result is illustrated in FIG. 2.

The performances of the two catalysts in Comparative Examples 1 and 2 are very similar. Both catalyst F-ATT-1 and KL7122 have an initial activity of about 85% conversion of MTBE, but they deactivate rapidly. After only about 80 hours on stream, the MTBE conversion was only about 20%.

Experiment 3

25.7 grams of the alumina-silica granules described in Comparative Experiment 2 are treated with an aqueous HF solution prepared by diluting 2.79 grams of 50% HF with 47.75 grams deionized water at ambient temperature for 1 hour with occasional stirring. The amount of HF used is approximately only 53.4% of that used in Comparative Example 1. After decanting out the excess solution, the alumina-silica granules are washed four times with 60 ml deionized water. After drying at 100° C. in a vacuum oven for 1 hour, the granules are calcined at 500° C. for 2 hours. This HF-treated amorphous silica alumina catalyst is referred to herein as "F-KL7122-1."

15 ml of F-KL7122-1 catalyst is tested in an identical manner to Comparative Example 1. The result is also illustrated in FIG. 2.

The initial activity of this catalyst is similar to the catalysts of Comparative Examples 1 and 2 (F-ATT-1 and KL7122). However, as shown in FIG. 2, the performance of this HF treated alumina-silica catalyst is superior to the comparative catalysts (F-ATT-1 and KL7122). It takes approximately twice the service time to reach the same degree of deactivation. Therefore, the fluorinated alumina-silica is an improved catalyst for decomposition of ethers such as MTBE.

Comparative Example 4

Another granular attapulgite clay (16-30 mesh) is calcined at 500° C. for 2 hours. A fluorinated attapulgite clay catalyst is prepared in a similar manner to Comparative Example 1.

32.2 grams calcined attapulgite clay granules is treated in an aqueous HF solution prepared by diluting 6.54 grams of 50% HF with 62.0 grams deionized water at ambient temperature for 1 hour with occasional stirring. After decanting out the excess solution, the clay is washed three times with 70 ml deionized water. The wet clay is dried at 100° C. in a vacuum oven for 1 hour and then calcined at 500° C. for 2 hours. This calcined catalyst is referred to herein as "F-ATT-2."

Figure 3:
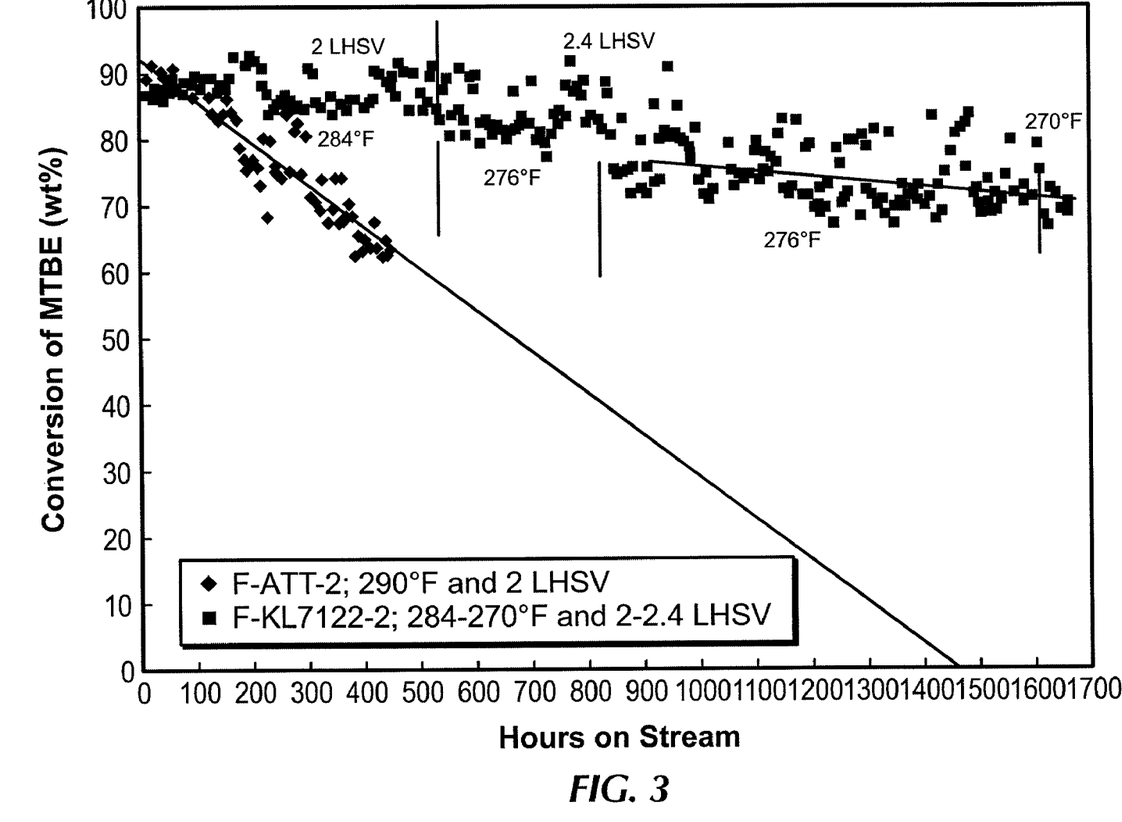
FIG. 3 is a graphical comparison of the catalyst activity, as measured by MTBE conversion, of catalysts according to embodiments disclosed herein as compared to prior art catalysts.

A high purity MTBE (99.69 wt. %) feed is decomposed over catalyst F-ATT-2. This MTBE feed contains no highly unsaturated compounds. The decomposition is carried out under similar conditions (31 psig, 290° F., 2.0 LHSV feed down-flow rate) as Comparative Example 1. The result of the decomposition is illustrated in FIG. 3.

The initial catalyst activity is about 90% MTBE conversion. The catalyst activity is much more stable compared with the F-ATT-1 catalyst of Comparative Example 1. Nevertheless, the experimental result predicts zero catalytic activity after about 1500 hours on stream. Commercially, the goal for MTBE conversion is typically about 65%, and the catalyst activity decreases below this conversion goal in about 400 hours.

Experiment 5

A fluorinated amorphous alumina-silica catalyst is prepared in a manner similar to Experiment 3, with a reduced quantity of HF. 26.92 grams of the alumina-silica granules described in Comparative Experiment 2 are treated with an aqueous HF solution prepared by diluting 2.02 grams of 50% HF with 47.18 grams deionized water at ambient temperature for 1.5 hours with occasional stirring. The amount of HF used is approximately only 37% of that used in Comparative Example 1. After decanting out the excess solution, the alumina-silica granules are washed four times with 60 ml deionized water. After drying at 100° C. in a vacuum oven for 1 hour, the granules are calcined at 500° C. for 2 hours. This HF-treated amorphous silica alumina catalyst is referred to herein as "F-KL7122-2." The physical properties of the catalyst are 312.0 m$^2$/g BET; 0.635 cc/g total nitrogen adsorption/desorption pore volume; and an average pore diameter of 8.15 nm.

15 ml of F-KL7122-2 catalyst is tested with the high purity MTBE used in Comparative Example 4. The initial start-up condition is 65 psig, 284° F. and 2.0 LHSV. Operating conditions were adjusted during the run as noted in the results as shown in FIG. 3.

The performance of this HF treated alumina-silica catalyst is superior to that of the clay catalyst in Comparative Example 4. There is little or no catalyst deactivation during the entire run (1659 hours). The projected life of this catalyst is at least one year or longer.

It is additionally noted that the HF treated alumina-silica catalysts described in Experiments 3 and 5, as compared to the clay catalysts, may be regenerated by calcining at a temperature in the range of 400° F. to 600° F. in air. The regenerability of the HF treated amorphous synthetic alumina-silica catalysts described herein may decrease the amount of waste produced due to catalyst replacement, among other advantages.

As described above, hydrofluoric acid treated amorphous synthetic alumina-silica catalysts as described herein may be useful for the decomposition of alcohols and ethers to form olefins. In a family of embodiments, the hydrofluoric acid treated amorphous synthetic alumina-silica catalysts as described herein may be useful for the decomposition of alkyl tertiary-alkyl ethers to form tertiary olefins, such as isobutylene, isoamylenes, and others.

Advantageously, embodiments disclosed herein may provide for a catalyst useful for decomposition reactions having an extended cycle length, deactivating over a period of up to 2 years or more in some embodiments. The extended service life may result in decreased olefin production costs, including decreased catalyst cost as well as decreased catalyst disposal costs. Additionally, embodiments of the catalysts described herein may have one or more of good physical integrity, a low attrition rate, and a high crushing strength. Further, manufacture of the catalysts described herein may use significantly decreased quantities of raw materials, such as hydrofluoric acid, as compared to prior art catalysts, thus reducing catalyst production and raw material disposal costs.

While the disclosure includes a limited number of embodiments, those skilled in the art, having benefit of this disclosure, will appreciate that other embodiments may be devised which do not depart from the scope of the present disclosure. Accordingly, the scope should be limited only by the attached claims.

What is claimed:

1. A process for the production of olefins from at least one of an alcohol and an ether, the process comprising:
    contacting at least one of an alcohol and an ether with a hydrofluoric acid-treated amorphous synthetic alumina-silica catalyst under decomposition conditions to produce an olefin;
    wherein the hydrofluoric acid-treated amorphous synthetic alumina-silica catalyst is produced by a process comprising:
        contacting an amorphous synthetic alumina-silica with a dilute hydrofluoric acid solution; and
        separating the dilute hydrofluoric acid solution from the catalyst;
        washing the catalyst to remove excess hydrofluoric acid.

2. The process of claim 1, wherein a ratio of hydrofluoric acid to amorphous alumina-silica during the contacting is in the range from greater than 0 g to about 65 g hydrofluoric acid per kg of alumina-silica.

3. The process of claim 1, wherein the hydrofluoric acid-treated amorphous synthetic alumina-silica catalyst comprises from about 2 weight percent to about 98 weight percent silica.

4. The process of claim 1, wherein the hydrofluoric acid-treated amorphous synthetic alumina-silica catalyst further comprises up to 10 weight percent of at least one of Ti, Zr, Hf, Ta, and Nb.

5. The process of claim 1, the process to produce the catalyst further comprising:
    calcining the catalyst at a temperature in the range of 300° C. to 850° C.

6. The process of claim 1,
    wherein the at least one of an alcohol and an ether comprises one or more of methyl tertiary butyl ether, tertiary butyl alcohol, sec-butyl methyl ether, ethyl tertiary butyl ether, tertiary amyl ethyl ether, diisopropyl ether, isopropyl alcohol, ethanol, and diethyl ether; and
    wherein the olefin comprises at least one of isobutylene, isoamylenes, propylene and ethylene.

7. The process of claim 1, wherein the contacting at least one of an alcohol and an ether is conducted in the presence of up to 5 weight percent water equivalents, based on a total amount of ether and water equivalents.

8. The process of claim 1, wherein the hydrofluoric acid-treated amorphous synthetic alumina-silica catalyst is selectively poisoned.

9. The process of claim 1, further comprising feeding a compound for the selective poisoning of the hydrofluoric acid-treated amorphous synthetic alumina-silica catalyst, wherein the contacting further comprises reacting an acid site on the hydrofluoric acid-treated amorphous synthetic alumina-silica catalyst with the selective poisoning compound.

10. The process of claim 1, wherein the process for generating the hydrofluoric acid-treated amorphous synthetic alumina-silica catalyst further comprises selectively poisoning the hydrofluoric acid-treated amorphous synthetic alumina-silica catalyst.

11. A process for the production of isobutylene from methyl tertiary butyl ether, the process comprising:
   feeding methyl tertiary butyl ether (MTBE) to a reactor having at least one reaction zone containing a hydrofluoric acid-treated amorphous synthetic alumina-silica catalyst;
   wherein the hydrofluoric acid-treated amorphous synthetic alumina-silica catalyst is produced by a process comprising:
      contacting an amorphous synthetic alumina-silica with a dilute hydrofluoric acid solution; and
      separating the dilute hydrofluoric acid solution from the catalyst;
   washing the catalyst to remove excess hydrofluoric acid;
   contacting the MTBE with the hydrofluoric acid-treated amorphous synthetic alumina-silica catalyst under decomposition conditions to produce a reactor effluent comprising isobutylene, unreacted MTBE, heavies, and methanol;
   feeding the reactor effluent to a first distillation column;
   separating the isobutylene from the unreacted MTBE, heavies, and the methanol in the first distillation column to recover a first bottoms fraction comprising heavies, unreacted MTBE, and methanol and an isobutylene-rich overheads fraction.

12. The process of claim 11, further comprising
   feeding the first bottoms comprising unreacted MTBE, heavies, and methanol to a second distillation column; and
   separating unreacted MTBE from the heavies and the methanol in the second distillation column to recover an MTBE-rich overheads fraction and a second bottoms comprising heavies and methanol.

13. The process of claim 12, further comprising recycling at least a portion of the MTBE-rich overheads to the reactor.

14. The process of claim 12, further comprising
   feeding the second bottoms comprising methanol and heavies to a third distillation column; and
   separating the methanol and the heavies to produce a methanol-rich overheads fraction and a heavies rich bottoms fraction.

15. The process of claim 11, wherein a ratio of hydrofluoric acid to amorphous alumina-silica during the contacting is in the range from about 5 g to about 65 g hydrofluoric acid per kg of alumina-silica.

16. The process of claim 11, wherein the hydrofluoric acid-treated amorphous synthetic alumina-silica catalyst comprises from about 2 weight percent to about 98 weight percent silica.

17. The process of claim 11, wherein the hydrofluoric acid-treated amorphous synthetic alumina-silica catalyst further comprises up to 10 weight percent of at least one of Ti, Zr, Hf, Ta, and Nb.

18. The process of claim 11, the process to produce the catalyst further comprising:
   calcining the catalyst at a temperature in the range of 300° C. to 850° C.

19. The process of claim 11, wherein the olefin comprises at least one of isobutylene, isoamylenes, propylene and ethylene.

20. The process of claim 11, further comprising feeding up to 1.5 weight percent water equivalents to the reactor, based on a total amount of MTBE and water equivalents.

21. The process of claim 11, wherein the hydrofluoric acid-treated amorphous synthetic alumina-silica catalyst is selectively poisoned.

22. The process of claim 11, further comprising feeding a compound for the selective poisoning of the hydrofluoric acid-treated amorphous synthetic alumina-silica catalyst, wherein the contacting further comprises reacting an acid site on the hydrofluoric acid-treated amorphous synthetic alumina-silica catalyst with the selective poisoning compound.

23. The process of claim 12, wherein the process for generating the hydrofluoric acid-treated amorphous synthetic alumina-silica catalyst further comprises selectively poisoning the hydrofluoric acid-treated amorphous synthetic alumina-silica catalyst.

* * * * *